United States Patent
Jeong

(10) Patent No.: US 7,950,071 B2
(45) Date of Patent: May 31, 2011

(54) FUNCTIONAL COMPRESSION SOCKS

(76) Inventor: Chang Min Jeong, Seoul (KR)

( * ) Notice: Subject to any disclaimer, the term of this patent is extended or adjusted under 35 U.S.C. 154(b) by 404 days.

(21) Appl. No.: 10/584,832

(22) PCT Filed: Dec. 30, 2004

(86) PCT No.: PCT/KR2004/003535
§ 371 (c)(1),
(2), (4) Date: Jun. 27, 2006

(87) PCT Pub. No.: WO2005/063062
PCT Pub. Date: Jul. 14, 2005

(65) Prior Publication Data
US 2007/0113593 A1    May 24, 2007

(30) Foreign Application Priority Data

Dec. 30, 2003  (KR) .................... 20-2003-0040568 U

(51) Int. Cl.
*A41B 11/00* (2006.01)
*A43B 17/00* (2006.01)
(52) U.S. Cl. .......................................................... 2/239
(58) Field of Classification Search ................ 2/61, 239,
2/240, 241, 242; 602/60, 61, 62, 63, 76;
66/178 R, 188, 178 A, 183, 182
See application file for complete search history.

(56) References Cited

U.S. PATENT DOCUMENTS

| | | | | |
|---|---|---|---|---|
| 967,585 | A | * | 8/1910 | Teufel .............................. 602/60 |
| 3,386,270 | A | * | 6/1968 | Simmons ..................... 66/178 A |
| 4,027,667 | A | * | 6/1977 | Swallow et al. ................. 602/63 |
| 4,522,044 | A | * | 6/1985 | Lineberry et al. .............. 66/185 |

(Continued)

FOREIGN PATENT DOCUMENTS

JP        11-124702        5/1999

(Continued)

OTHER PUBLICATIONS

Hatch, Kathryn L., Textile Science, West Publising Company, p. 279.*

(Continued)

*Primary Examiner* — Alissa L Hoey
*Assistant Examiner* — Amber R Anderson
(74) *Attorney, Agent, or Firm* — Kile Park Goekjian Reed & McManus PLLC

(57) ABSTRACT

This invention relates to functional socks which provide appropriate and variable compression on the various parts of foot.

The functional compressive socks of this invention comprise the parts including shin, calf, instep, toe, heel, and sole. The said socks are characterized by the fact that all those said parts are subject to appropriate compression by part, and in addition, the said parts of shin, calf, instep, and sole are knitted with high elasticity yarn as the elastic threads and the core yarn single covered with polyurethane based long staple or long staple copolymer fiber as the inner threads, while the said parts of toe and heel are knitted with the core yarn single covered with polyurethane based long staple or long staple copolymer fiber as the inner threads, in appropriate ratio set respectively by the characteristics of the part.

According to this invention which utilizes high elasticity yarn and implements a multi-stage compressive knitting technology that can adjust the lateral tensile force of the elastic threads, the blood in foot is pressed bilaterally promoting the circulation, therefore, the socks which can prevent or even treat the varix or edema can be produced.

20 Claims, 15 Drawing Sheets

U.S. PATENT DOCUMENTS

| | | | | |
|---|---|---|---|---|
| 4,898,007 A | * | 2/1990 | Dahlgren | 66/185 |
| 5,617,745 A | * | 4/1997 | Della Corte et al. | 66/178 A |
| 6,012,177 A | * | 1/2000 | Cortinovis | 2/239 |
| 6,092,397 A | * | 7/2000 | Cortinovis | 66/184 |
| 6,223,782 B1 | * | 5/2001 | Watkins | 139/383 R |
| 6,240,716 B1 | * | 6/2001 | Yanagawase et al. | 57/210 |

FOREIGN PATENT DOCUMENTS

| | | |
|---|---|---|
| JP | 11-323607 | 11/1999 |
| JP | 2002-327306 | 11/2002 |
| KR | 2000-70540 | 11/2000 |
| KR | 0271214 | 4/2002 |
| WO | 2005/063062 | 7/2005 |

OTHER PUBLICATIONS

International Search Report for International Application No. PCT/KR2004/003535 dated May 26, 2005.

* cited by examiner

[ SOLID DRAWING ]

(A-1), (A-2), (B), (C)
: MULTISTEP GRADATIONAL HIGH COMPRESSION TEXTURE

FUNCTIONAL COMPRESSION SOCKS

TECHNICAL FIELD

This invention relates to the knitting of socks, which especially has the functionality of giving appropriate compression on all surfaces of foot.

In this invention, the parts including shin(11), calf(14), instep(12) and sole(15) are made from yarn single covered with polyurethane based long staple or long staple copolymer fiber, and from lycra soft yarn, which is highly elastic, double covered separate nylon 70/D/24F/1 high speed textured yarn, at optimum conditions. Thus the expansibility of the lycra soft yarn which is the wadding thread is maintained, and the strong force of restitution of the lycra soft yarn is utilized, which is the characteristics of the lycra soft yarn. Therefore, two different characteristics of the same yarn material are utilized by using the nylon 70D/24F/1 as the high speed textured yarn and the double covered lycra soft yarn applied with covering technology for highly elastic yarn. In textile industry, 70D/24F/1/is a well-known terminology and stands for 70D(denier)/24F(filament)/1(single yarn), wherein D(denier) refers to a weight per length of filament thread and expresses the thickness of long filament thread, with 1D being defined as 1 g in weight per 9000 m length of thread and 70D means a weight of 70 g per 9000 m. Therefore, 70D/24F/1 means a single yarn having a thickness of 70D and consisting of 24 strands. That is, the thickness of the single yarn becomes 70D by joining 24 strands together, thickness of each strand being 2.916666D.

As for the knitting technology, using high elastic yarn gradually from the sole part(15) up to the shin part(11) provides gradual compression in accordance with the shape of leg by the tensile force exerted by the yarn in horizontal plane, which is the multi stage compressive knitting technology. In addition, by applying the knitting technology which enables gradual decompression, using elastic yarn as the rib, in 1:1, 2:2, or 3:1 ratio for example, from the sole(15) to the shin(11), thus, the shin part(11) shall be configured to be in a jar-like shape which is suitable for the body shape as well as providing an artificial skin having high elastic functionality giving soft but tight compression when worn, promoting blood circulation up to the leg by physical effect preventing, or even curing, varix and edema.

Additionally, the knitting and heat treatment technology, such as piece dyeing, enhance the elasticity of the said yarn.

And by using lycra soft yarn, by double covering method, and by winding separate nylon 70D/24F/1 high speed textured yarn with double covering method at optimum conditions, enable using general elastic yarn feeding device without the slip prevention device which is exclusively used for the polyurethane yarn, which in turn enables mass production with lower cost.

Additionally, by using said high elastic yarn, the restitution force of the lycra soft yarn can be maximized while maintaining its expansibility at an appropriate level by the application of the double covering technology in order to provide strong tightness solving the problems incurred by using latex based double covering yarns which is the most general material used for producing socks, providing a higher level of physical characteristics—soft but strong restitution force.

As for the parts where the high elastic yarn is used. It is not a specific part but all over the sock that makes use of the said highly elastic yarn. The optimum tightness in accordance with the body shape is obtained by the speed control of the yarn at the sock knitting machine, implementing multi-stage compression knitting technology all over the sock except the heel and toe, propelling the blood stream in foot up to the heart. Therefore, for the knee-high socks, medical-care-type socks can be produced preventing and curing the varix and edema.

This invention is characterized by utilizing the strong force of restitution and lower expansibility yarn with the implementation of multi-stage compression technology for producing socks.

BACKGROUND ART

In this convention, as for the shin part(11), calf part(15), instep part(12), and sole part(15), with inner threads made with yarn single covered with polyurethane long staple or long copolymer fiber, and separate nylon 70D/24F/1 high speed textured yarn wound on highly elastic lycra soft yarn by double covering method at optimum conditions, maintaining the expansibility of the lycra soft yarn which is the wadding thread, providing and utilizing the strong force of restitution which is the characteristics of the lycra soft yarn, with the covering technology of lycra soft yarn double covered with nylon 70D/24F/1 high speed textured yarn, providing the same kind but different characteristics, and by using the said highly elastic yarn as the elastic yarn gradually from the sole(15) up to the shin part(11) with the application of multi-stage compression knitting technology in accordance with the leg shape, with elastic yarn rib fabrication in 1:1, 2:2, or 3:1 for gradual decompression from sole(15) to the shin(11), giving the jar-like shape at the shin part(11).

Consequently, the socks produced by the art of this invention have the shape fit for the leg as well as the characteristics of an artificial functional skin giving soft but strong tightness promoting the blood flow in foot by elastic compression, preventing and curing the varix and edema, a knitting design technology based on human engineering.

By adding the heat treatment technology such as piece dyeing, the high elasticity of the product is further enhanced.

In addition, by winding separate nylon 70D/24F/1 high speed textured yarn by the double covering method at optimum conditions on lycra soft yarn, general elastic yarn feeding devices can be used without separate slip prevention devices which are required exclusively for polyurethane yarn, enabling mass production at lower production cost. And by using the said highly elastic yarn in order to make use of the restitution force which is the characteristics of the lycra soft yarn, while maintaining(restraining) appropriate expansibility by double covering technology, in order to solve the problems in using the double covering yarn of latex based material which is the general material of socks, providing a higher grade physical characteristics(soft and strong elasticity).

As for the parts where the high elastic yarn is used, it is not a specific part but all over the sock that makes use of the said highly elastic yarn. The optimum tightness in accordance with the body shape is obtained by the speed control of the yarn at the sock knitting machine, implementing multi-stage compression knitting technology all over the sock except the heel and toe, propelling the blood stream in foot circulate back to the heart. Therefore, for the knee-high socks, medical-care-type socks can be produced preventing and curing the varix and edema.

This invention is characterized by utilizing the strong force of restitution and lower expansibility yarn with the implementation of multi-stage compression technology for producing socks.

DISCLOSURE

Technical Problem

In general, three basic types of yarn comprising inner thread, outer thread, and elastic thread are used in knitting socks.

A wide variety of materials can be used for outer thread according to the specific purpose of the product, for example, cotton, wool or acryl for warmness. Though such many kinds of materials are being used, they are only for simple knitting added with a touch of fashion utilizing the material characteristics.

Regarding the inner thread, also a wide diversity of materials are being used including nylon, spandex, highly elastic polyester, etc.

In general, the elastic yarn in socks is the double covered elastic yarn(#90, #110) made of latex, used at the top for a length of 1.5 cm to 4.5 cm which is a common and basic feature of most socks. In sports socks or functional socks, the double covered elastic yarn of latex based is used in the sole of socks for a length of 4 cm to 4.5 cm to prevent slip down or to provide tension.

In case of the conventional functional socks which utilize the latex based double covering elastic yarn, due to the lower elasticity of sock fabric, the inconvenience of separation and slip between the socks and skin during a long-term activity, sports activity or mountain climbing, even without sweat. And if sweated, the separation becomes severe causing physical troubles which may compel changing the socks, if kept worn, may cause physical damage to the skin(peeling, blisters) as well as degradation in the protective function. In sports activities, the sense of motion and physical ability may be degraded.

As a matter of fact, the functions of conventional socks are; physical protection of feet, keeping warm in cold, and absorbing sweat or humidity, which are rather simple 'covering of foot'.

In recent days, as it has been known that the feet play important role for body health, functional socks having specific minerals such as copper, silver, or a certain kind of mineral in their yarn, or attaching magnetic materials on socks by a special process, for the purpose of antibiotics/antistench property, or socks with enhanced physical characteristics including absorbability or heat insulation by improving the physical features of the yarn has been developed and produced.

However, in general, mostly socks have been knitted with lower elasticity latex or spandex for elasticity, partially using double covering elastic yarn, and mostly using nylon or general polyurethane material yarn, which are chemical fiber having lower elasticity.

The functionality of general socks is described hereunder referring to the Drawing 1.

Drawing 1 shows the perspective view of a common sock.

As shown in the Drawing 1, as for the toe(2), sole(3), and heel(4), the toe(2) and heel(4) part are knitted in solid to absorb sweat, latex based double covering elastic yarn is partially used in instep(5), bottom ankle(6), and ankle(7) for elasticity, while other parts are mostly knitted with lower elasticity chemical fiber such as nylon or polyurethane comprising the based of sock.

Due to the fact that the latex based double covering elastic yarn is used at specific parts only, problems including poor appearance, blood stream blocking cause by compressing a narrow width of body, after-trace by tightness, or itching may be incurred. Generally, elastic yarn is knitted in the ankle part of socks loosely.

As a matter of fact, in some sports activity socks, general latex based double covering elastic yarn is knitted in the sole or ankle part to provide relatively better elasticity, to be named as a functional sock.

Furthermore, lycra soft yarn having high elasticity is being generally used, without additional processing, using a separate polyurethane yarn feeding device, a special equipment preventing slip at yarn feeding for sock production.

The socks produced in this method shows the characteristics of the lycra soft yarn(520 denier), restitution force and expansibility stronger than general yarn.

However, even the recreation/sports socks knitted with lycra soft yarn(520 denier) sometimes require limited expansibility, which is not possible for lycra soft yarn(520 denier) socks.

In addition, due to the structure and characteristics of elastic yarn feeding device of general sock knitting machine where lycra soft yarn slips, it is difficult to weave socks as desired.

As shown in drawing 1, the main body of general socks can absorb humidity and prevent themselves from slipping down, however, it is necessary for socks to exert appropriate compressive force(tightness) on ankle and instep parts for edema patients, for an extreme case, or workers who have to be standing for a long time to solve the blood flow problem in feet. As described hereinabove, general socks can only cover up the feet, due to the limit in material and knitting technology.

The object of this invention is the technology which enables control of knitted tension in lateral direction of socks by distributing appropriate tensile force of highly elastic yarn in multi-stages, in order to produce functional socks which promote blood flow in feet by compressing the blood in bilateral direction.

Technical Solution

In order to implement abovementioned technical goal, this invention utilizes the yarn single covered with polyurethane series long fiber for the shin part(11), calf(14), instep(12), and sole(15), or long copolymer fiber as inner thread incorporating separate nylon 70D/24F/1 high speed textured yarn double covered on lycra soft yarn which highly elastic, in order to maintain the expansibility of the lycra soft yarn which is the wadding thread, and utilizing the strong force of restitution of the lycra soft yarn which is a characteristics of lycra soft yarn, thus, enabling the highly elastic lycra soft yarn, double covered with nylon 70D/24F/1 high speed textured yarn, also enabling the same type but different characteristics yarns to be used, as the elastic yarn.

As for the knitting technology, by knitting highly elastic yarn gradually from sole(15) to shin(11) implementing multistage compression by lateral tensile force of the elastic yarn, in accordance with the shape of legs, while knitting the elastic yarn fabrication as a rib structure in the ratio of 1:1, 2:2, 3:1 in accordance with the leg shape to provide gradual compression strength from sole(15) to shin(11), shaping the shin part(11) as a jar-like figure which is fit for leg structure, as well as giving soft and tight sense of wear functioning as an artificial skin, promoting blood flow in feet, preventing and curing varix or edema.

Additionally, the knitting and heat treatment technology, such as piece dyeing, enhance the elasticity of the said yarn.

And by using lycra soft yarn, by double covering method, and by winding separate nylon 70D/24F/1 high speed textureded yarn with double covering method at optimum conditions, enable using general elastic yarn supply device without the slip prevention device solely for the polyurethane yarn, which in turn enables mass production with lower cost.

Additionally, by using said high elastic yarn, the restitution force of the lycra soft yarn can be maximized while maintaining its expansibility at an appropriate level by the application of the double covering technology in order to provide strong tightness solving the problems incurred by using latex based double covering yarns which is the most general material used for producing socks, providing a high level of physical characteristics—soft but strong restitution force.

As for the parts where the high elastic yarn is used. It is not a specific part but all over the sock that makes use of the said highly elastic yarn. The optimum tightness in accordance with the body shape is obtained by the speed control of the yarn at the sock knitting machine, implementing multi-stage compression knitting technology all over the sock except the heel and toe, propelling the blood stream in foot up to the heart. Therefore, for the knee-high socks, medical-care-type socks can be produced preventing and curing the varix and edema. This invention is characterized by utilizing the strong force of restitution and lower expansibility yarn with the implementation of multi-stage compression technology for producing socks.

ADVANTAGEOUS EFFECTS

According to this invention, by implementing multi-stage compression knitting technology controlling the lateral tensile force of lateral elastic thread, promotes the blood flow in feet by giving bilateral pressure on veins, and enables the production of medi-care type socks preventing or curing the varix or edema.

In addition, by compressing ankles with high elasticity, ankles can be protected by socks acting as ankle protective band.

Socks produced by this invention also can prevent the heat accumulation in the sock by absorbing the heat and emitting the heat out, reducing the stuffy sense of feet caused by high temperature.

Figure 1:
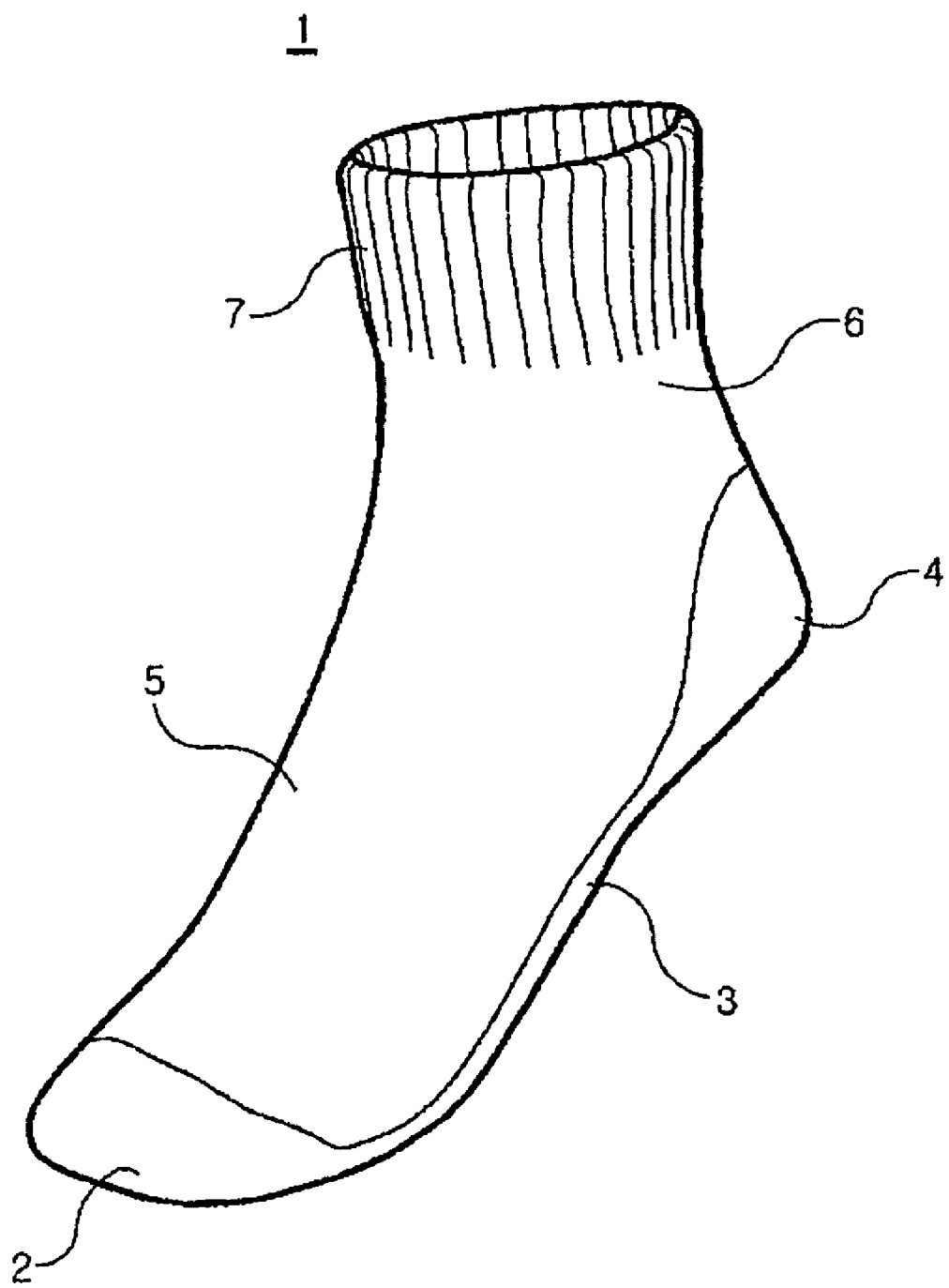
FIG. 1 illustrates a perspective view of a generic sock.

| 11 | Shin Part | 12 | Instep Part |
|----|-----------|----|-------------|
| 14 | Calf Part | 15 | Sole Part |
| 16 | Heel Part | 17 | Toe Part |

BEST MODE

Using highly elastic yarn, establish the knitted tensile strength of lateral elastic yarn in multi stages. Implementing step compressive knitting technology to give bilateral pressure to the blood in the foot, long-necked socks can promote the blood circulation.

MODE OF INVENTION

In order to accomplish abovementioned technical goal, the functional compressive solid long-necked socks produced by the art of this invention aim at maintaining appropriate pressure according to the parts of a foot comprising shin, calf, instep, toe, and heel, wherein, highly elastic yarn is knitted in the shin, heel, instep, and sole, and using yarn single covered with polyurethane series long staple or long staple polymer fiber as the inner threads, knitted in proper ratio, and the toe and heel are knitted with polyurethane series long staple or long staple polymer fiber as the inner threads, which is one of the characteristics of this invention.

And, the said highly elastic yarn is characterized that it is the lycra soft yarn double covered with nylon 70D/24F/1 high speed textured yarn.

And, as for the said long staple fiber, it is characterized that one of those polyamide fiber, polyester fiber, or polypropylene fiber is used.

And, this invention is also characterized by knitting the said shin and instep parts with rib structure comprising elastic yarn and inner thread at 2; 2 ratio, while the said calf and sole parts are knitted in rib structure with elastic yarn and inner thread at 1:1 ratio.

And, the said toe and heel parts are characterized by being knitted in solid structure.

And, the said toe and heel parts are characterized by being knitted in solid structure.

Detailed description of this invention is set forth hereinafter, referring to the drawings.

Figure 2:
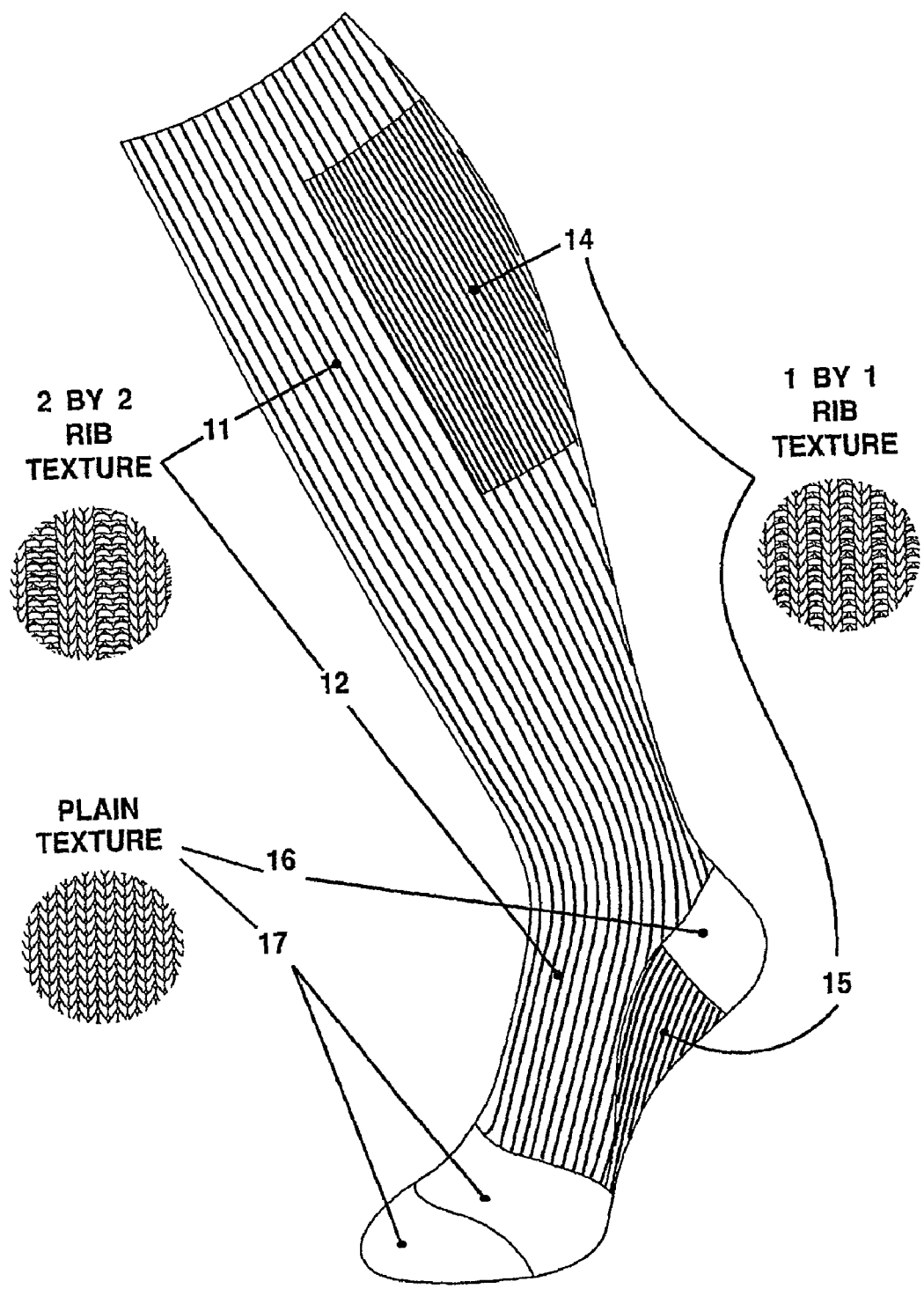
FIG. 2 illustrates a perspective view of a functional compressive long-necked sock produced by the art of this invention.

FIG. 2 illustrates a functional compressive long-necked sock which is an embodiment of this invention, comprising shin(11), calf(14), instep(12), toe(17), heel(16), and sole(15).

The said shin(11), calf(14), instep(12), and sole(15) parts are knitted with highly elastic yarn as the elastic yarn and yarn single covered with polyurethane series long staple or long staple polymer fiber as the inner thread.

In order to prevent twisting and to maintain elasticity, the yarn double covered with nylon 70D/24F/1 by S twist or Z twist is used, while the core yarn is the polyurethane series lycra soft 520 denier.

And, the said toe(17), heel(16) parts do not make use of highly elastic yarn but use the core yarn single covered with polyurethane series long staple or long copolymer fiber as the inner threads for knitting. Therefore, these parts are not compressed enabling free movement and smooth blood circulation of the toe.

As for the said long staple, one of the polyamide fiber, polyester fiber, or polypropylene fiber may be used.

The said shin(11) and instep(12) parts are knitted in 2:2 rib structure, said calf(14) and sole(15) parts are knitted in 1:1 rib structure, and the said toe(17) and heel(16) parts are knitted in solid structure. The compressive forces on the instep(12) and sole(15) are exerted in the direction of blood flow by the structural characteristics of the rib structure allowing uninterrupted flow of blood.

And, the said instep(12) and sole(15) parts are knitted in 2:2 and 1:1 rib structure respectively, giving the compression on the instep(12) stronger and softer than that on the sole(15).

The lower part of the shin(11) is knitted in 2:2 rib structure providing rather stronger compression, which is very effective for protecting the ankle which is liable to be easily injured.

It is not necessary to use any compress on the lower shin which is knitted in 2:2 rib structure, providing better appearance, easier than general or other type of functional socks to wear and take off shoes.

In addition, said shin(11) part is knitted in 2; 2 rib structure for stronger compression, while the calf(14) part is knitted in 1:1 rib structure for weaker compression than that of the shin(11).

Figure 3:
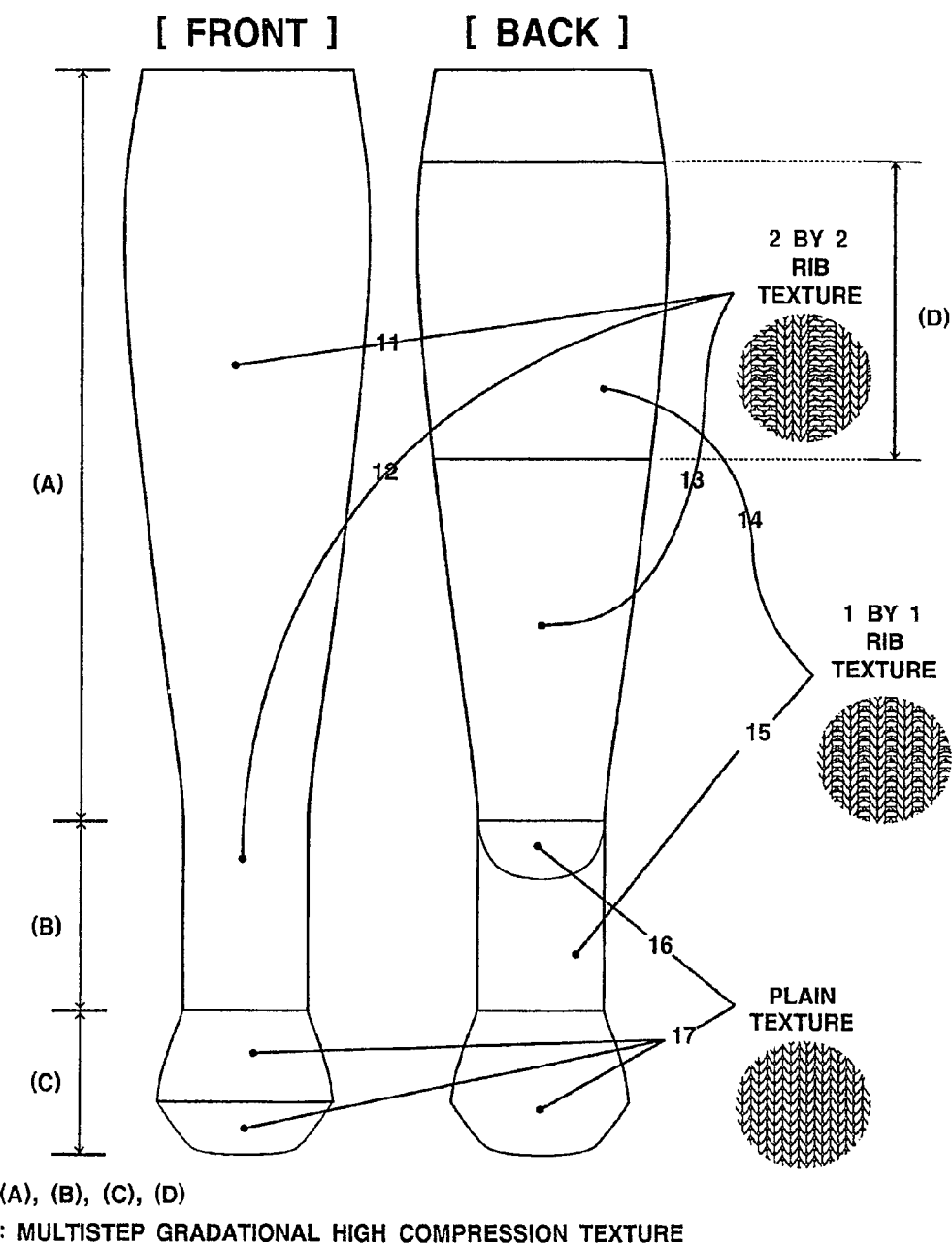
FIG. 3 illustrates a front and rear view of a functional compressive long-necked sock produced by the art of this invention.

FIG. 3 illustrates a front and rear view of the functional compressive long-necked sock produced by the art of this invention.

Figure 4:
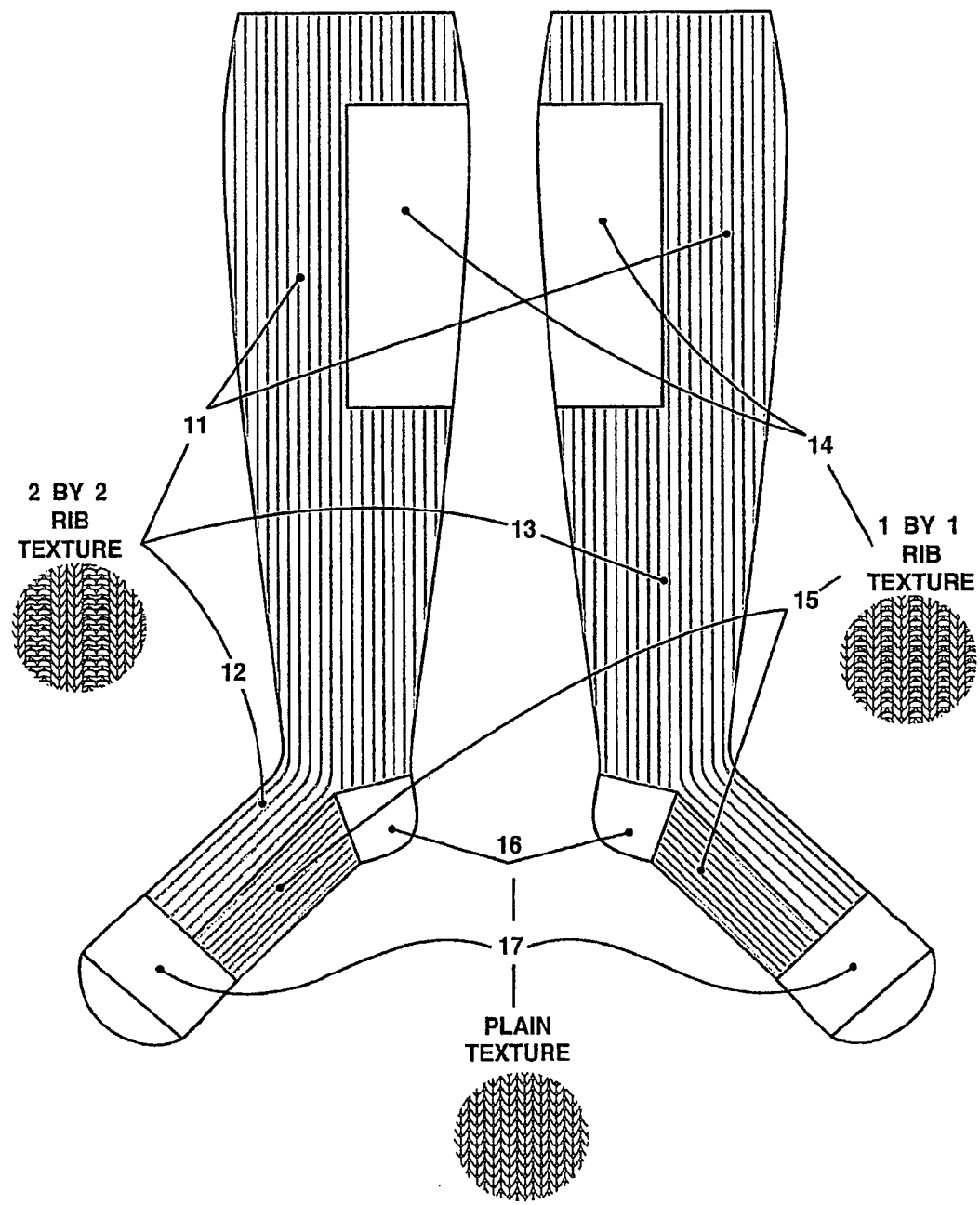
FIG. 4 illustrates a left and right side view of a functional compressive long-necked sock produced by the art of this invention.

FIG. 4 illustrates a side view of the functional compressive long-necked sock produced by the art of this invention, of which the shin(11) part is divided into three parts according to the width of the elastic yarn.

As for the knitting method of the shin(11) of the said long-necked sock, dividing it into three blocks, according to the width of the elastic yarn, which are knitted by application of multi stage compression technology grading the lateral tensile strength of the high elasticity yarn in multiple steps, the part(11) is shaped in a jar-like appearance which is suitable for the shape of leg that provides soft and tight compression by the parts of a foot, acting as an functional, artificial, elastic skin.

Figure 5:
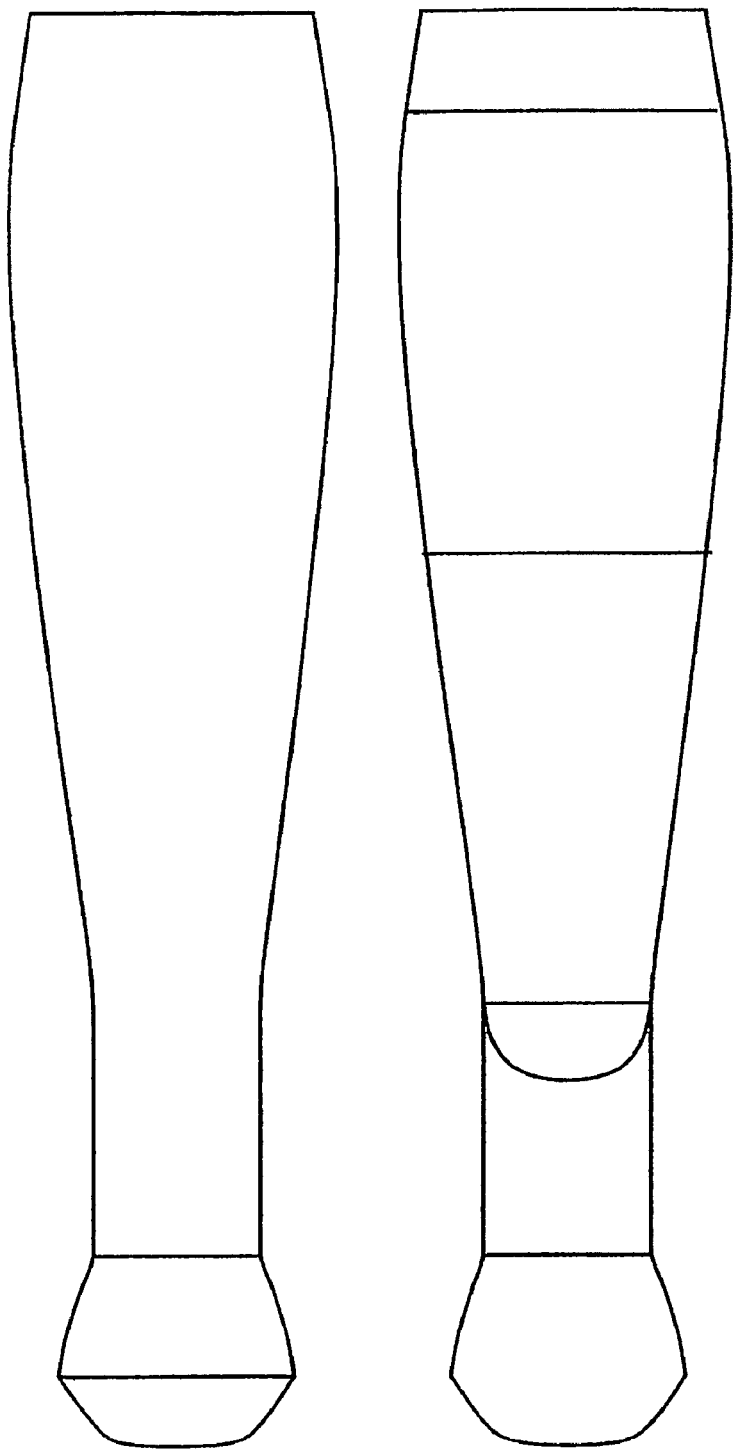
FIG. 5 illustrates a front and rear view of the inside of a functional compressive long-necked sock produced by the art of this invention.

FIG. 5 illustrates an inside structure of the functional compressive long-necked sock produced by the art of this invention, presenting from the sole to the top of the shin.

In the FIG. 5 showing the inside, by using high elasticity yarn gradually from the sole(15) to the shin(11) and by multi stage compressive knitting achieved by controlling lateral tension of the yarn in accordance with the shape of leg, therefore, the gradual decompression from sole(15) to shin (11) physically promotes up-flow of blood, preventing or even curing the varix and edema. As for the method of obtaining and maintaining the compression by knitting high elasticity yarn in concordance with the leg shape, in a general sock knitting machine without a drum device under the machine bed, using rollers and stepping motor for double covering yarn by each course section, on the basis of yarn knitting product, by controlling the lateral knitting speed of the yarn in multiple steps in accordance with the parts to produce socks having part sizes fit for legs, and by using high elastic yarn all over the sock, high elastic socks having shape fit for legs and exerting multi stage compression could be implemented.

As for the knitting of the high elasticity yarn on the front of the ankle, which has been impossible for the conventional knitting technology, the visual problem cause by 1-2 course omission when knitting from the sole up to the ankle could be solved technically. Therefore, it is possible to weave socks from sole to shin with said high elasticity yarn replacing the elastic yarn double covered with general latex base material, which gives enhanced wearing sense as well as various physical advantages which those products made with elastic yarn double covered with latex base material.

However, in case that a little stronger elasticity than common socks is required, not so much as the strong elasticity acquired by this invention, the double covering yarn of latex base which is generally used in common socks, or common polyurethane yarn, or the lycra soft yarn which is a high elasticity yarn made of polyurethane, may be utilized as the wadding threads and using the core yarn double covered with nylon 70D/24F/1 high speed textured yarn with the same knitting technology set forth in this invention to produce products having various characteristics.

Figure 6:
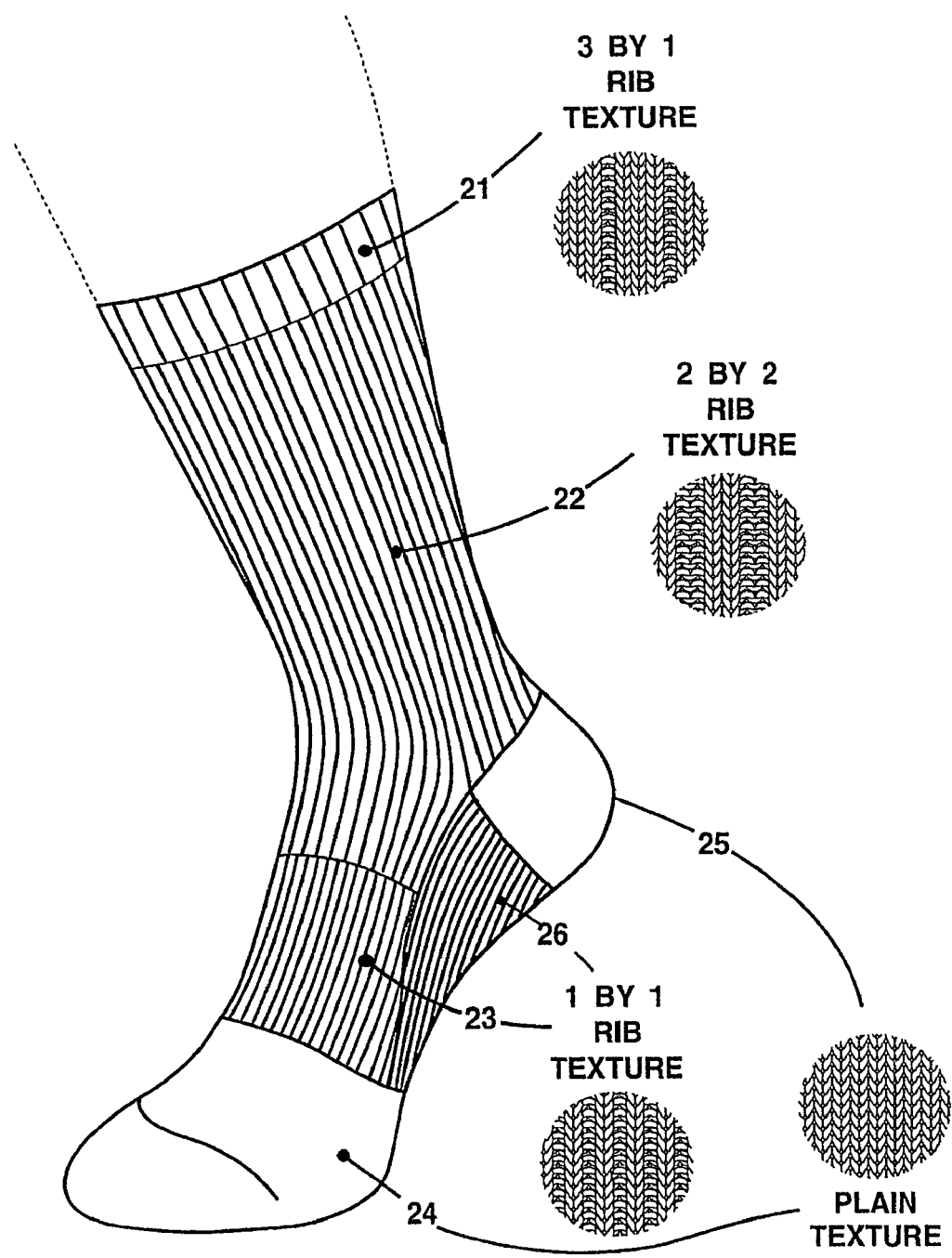
FIG. 6 illustrates a perspective view of a functional compressive medium-necked sock produced by the art of this invention.

FIG. 6 illustrates an embodiment of this invention as a functional compressive medium-necked sock comprising the tightening part(21) at the inlet, ankle(22), instep(23), toe(24), heel(25), and the sole(26).

The tightening part(21) at the inlet, ankle(22), instep(23), and the sole(26) parts are knitted with high elastic yarn as the elastic thread and the core yarn single covered with polyurethane long staple or the long staple of copolymer fiber as the inner threads.

The said high elasticity yarn is the core yarn double covered with nylon 70D/24F/1 high speed textured yarn in S twist or Z twist for the prevention of twisting and the maintenance of elasticity, and the said core yarn is the polyurethane series lycra soft 520 denier.

And the toe(24) and heel(25) are knitted with the core yarn single covered with polyurethane series long staple or long staple copolymer fiber as the inner threads.

One of the polyamide, polyester, or polypropylene fiber is used for the said long staple copolymer fiber.

The desirable knitting structures by parts are: 3:1 rib structure for the tightening part(21), 2:2 rib for ankle(22), 1; 1 rib for instep(23) and sole(26), and solid structure for toe(24) and the heel(25).

Figure 7:
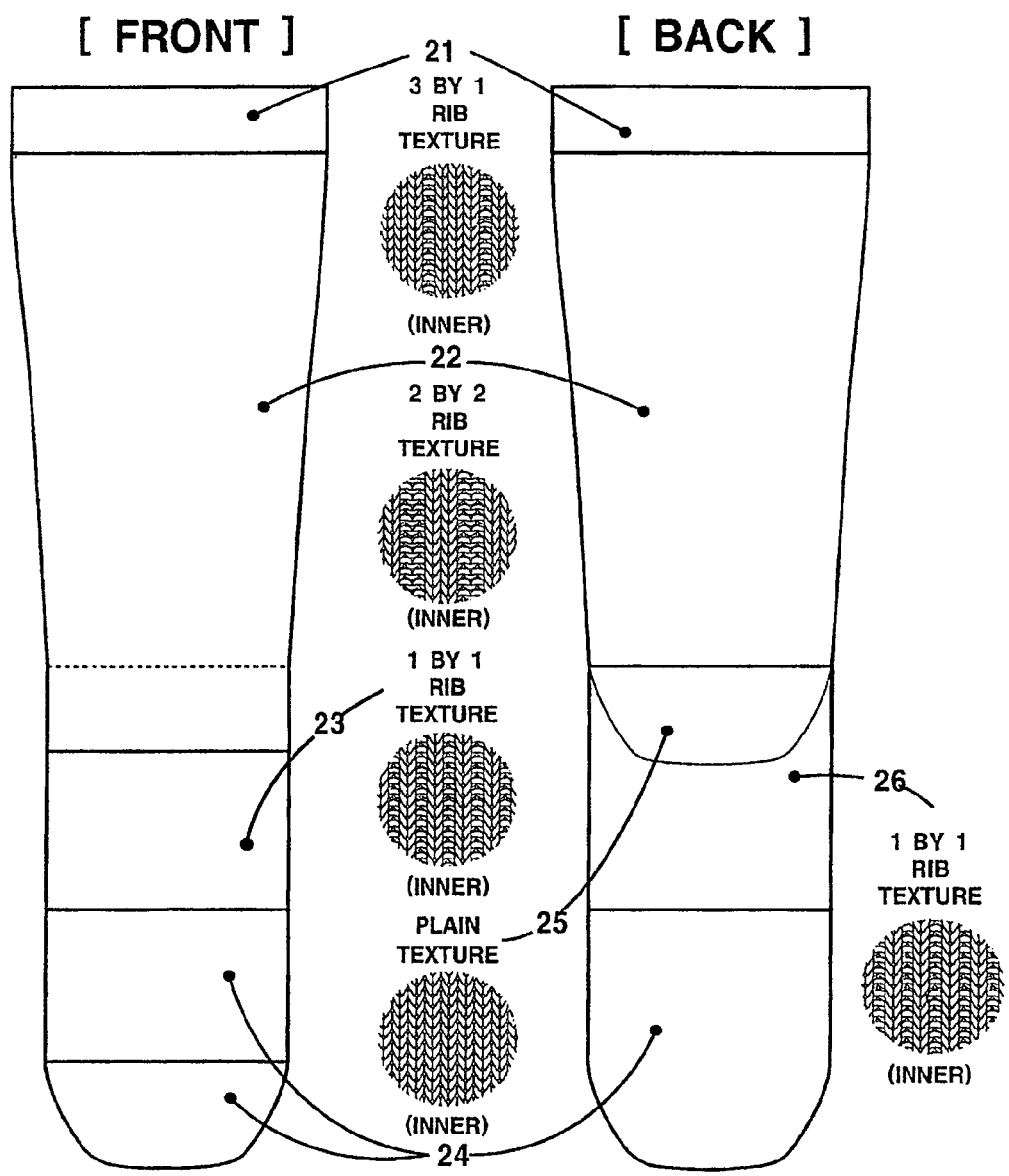
FIG. 7 illustrates a front and rear view of inside of a functional compressive medium-necked sock produced by the art of this invention.

FIG. 7 illustrates a front and rear view of a functional compressive short-necked sock produced by the art of this invention.

Figure 8:
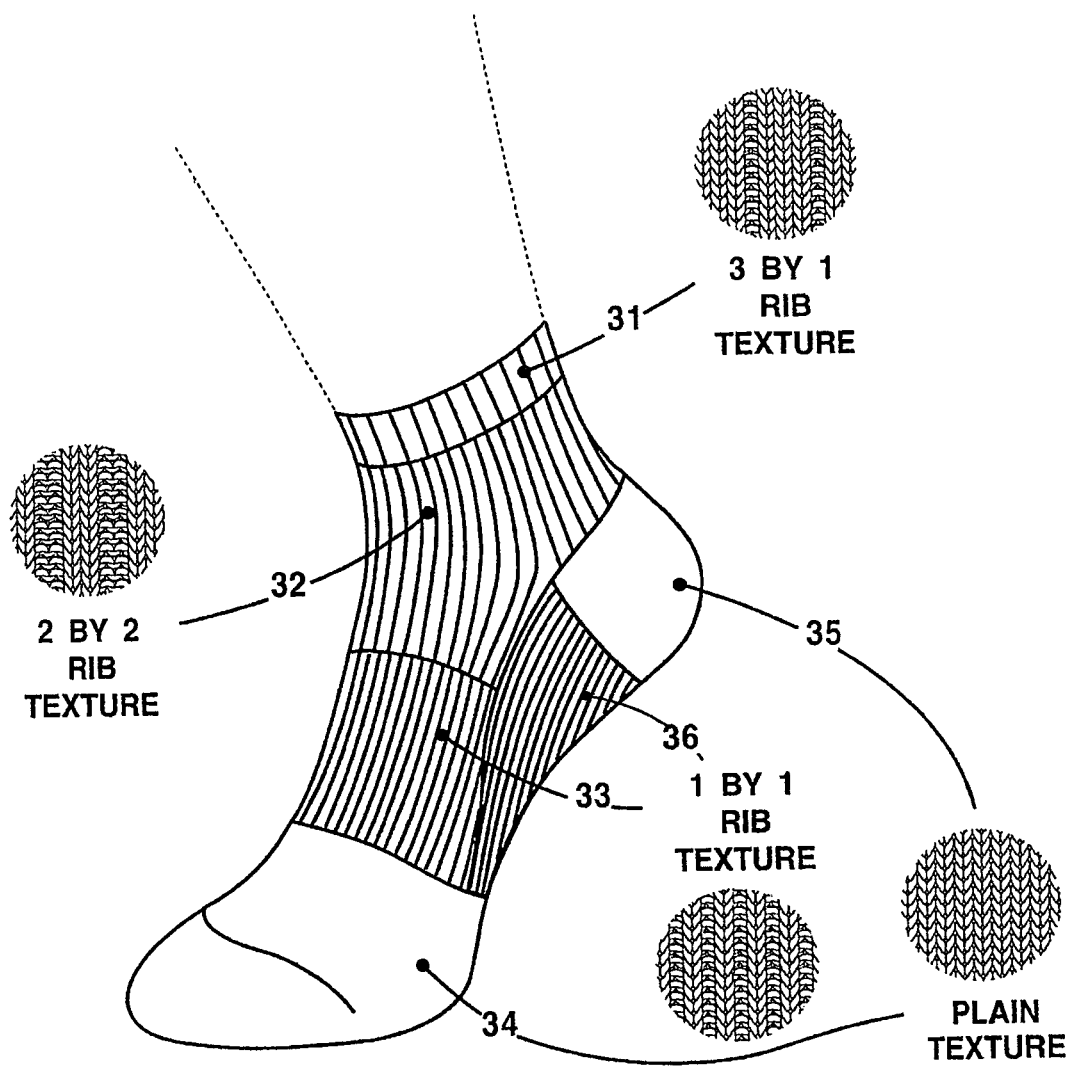
FIG. 8 illustrates a perspective view of a functional compressive short-necked sock produced by the art of this invention.

FIG. 8 illustrates an embodiment of this invention as a functional compressive short-necked sock, comprising tightening part(31) at the inlet, bottom ankle(32), instep(33), toe (34), heel(35), and sole(36) parts.

The tightening part(31) at the inlet, bottom ankle(32), instep(33), and the sole(36) parts are knitted with high elastic yarn as the elastic thread and the core yarn single covered with polyurethane long staple or the long staple of copolymer fiber as the inner threads.

The said high elasticity yarn is the core yarn double covered with nylon 70D/24F/1 high speed textured yarn in S twist or Z twist for the prevention of twisting and the maintenance of elasticity, and the said core yarn is the polyurethane series lycra soft 520 denier.

And the toe(34) and heel(35) are knitted with the core yarn single covered with polyurethane series long staple or long staple copolymer fiber as the inner threads.

One of the polyamide, polyester, or polypropylene fiber is used for the said long staple copolymer fiber.

One of the polyamide, polyester, or polypropylene fiber is used for the said long staple copolymer fiber.

The desirable knitting structures by parts are: 3:1 rib structure for the tightening part(31), 2:2 rib for bottom ankle(32), 1; 1 rib for instep(33) and sole(36), and solid structure for toe(34) and the heel(35).

Figure 9:
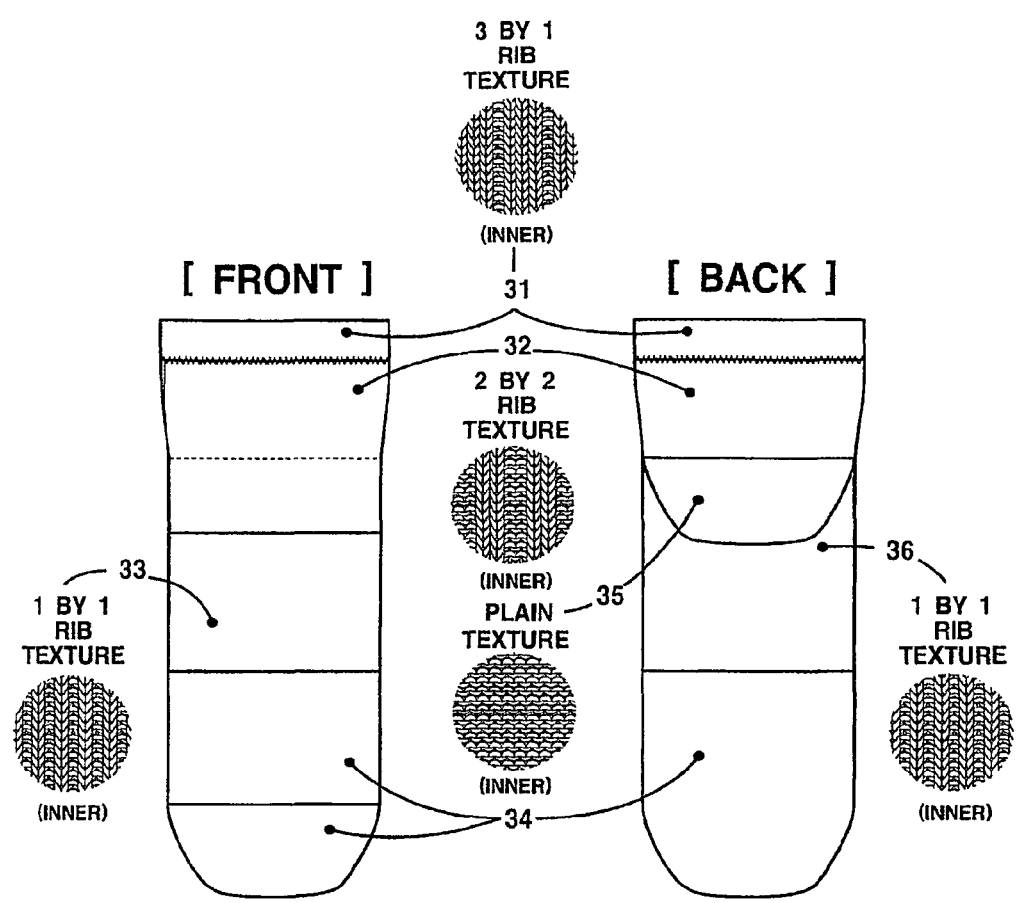
FIG. 9 illustrates a front and rear view of inside of a functional compressive short-necked sock produced by the art of this invention.

FIG. 9 illustrates a front and rear view of a functional compressive short-necked sock produced by the art of this invention.

Figure 10:
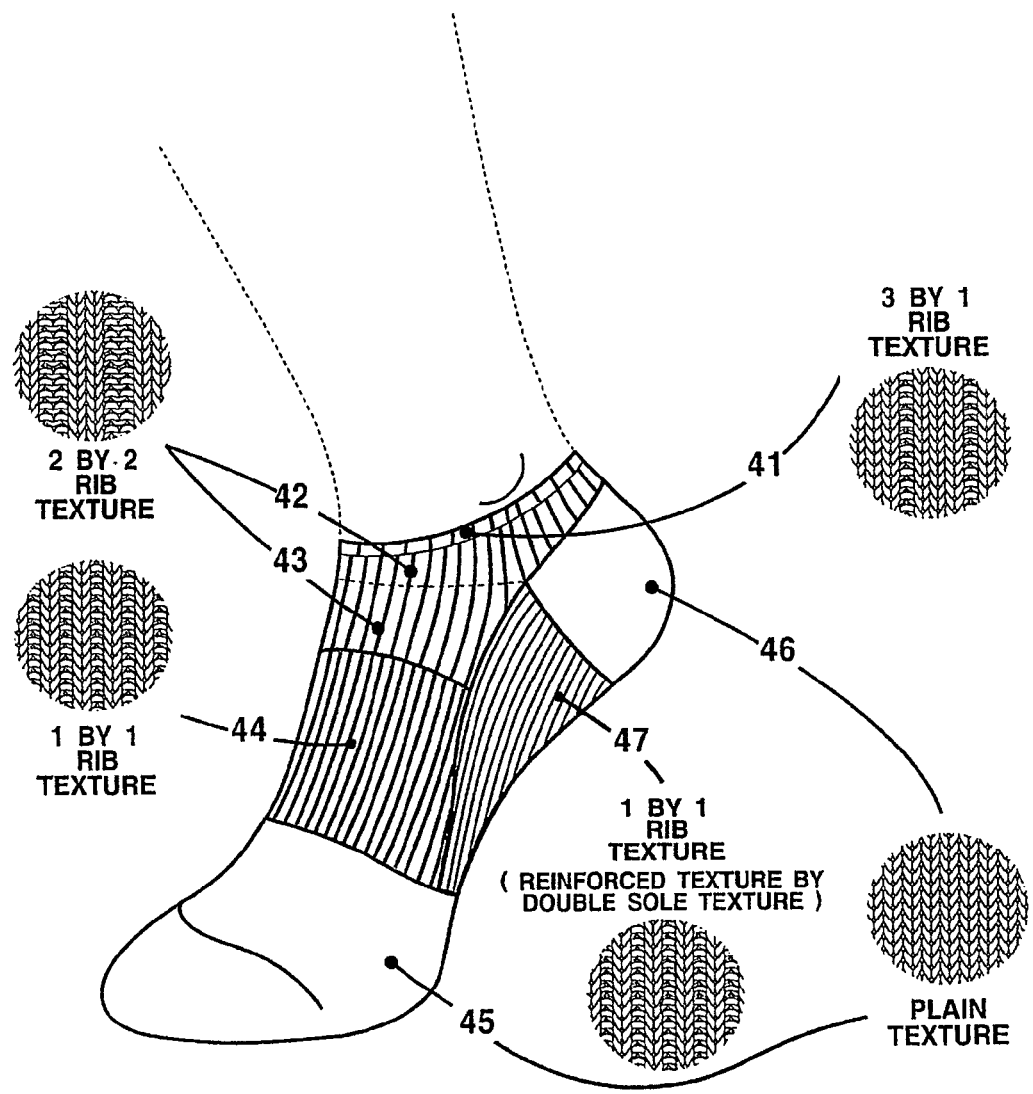
FIG. 10 illustrates a perspective view of a functional compressive nude sock produced by the art of this invention.

FIG. 10 illustrates an embodiment of this invention as a functional compressive nude sock, comprising tightening part(41) at the inlet, bottom ankle(42), first instep(43), second instep(44), toe(45), heel(46), and sole(47) parts.

The tightening part(41) at the inlet, bottom ankle(42), first instep(43), second instep(44), and the sole(47) parts are knitted with high elastic yarn as the elastic thread and the core yarn single covered with polyurethane long staple or the long staple of copolymer fiber as the inner threads.

The said high elasticity yarn is the core yarn double covered with nylon 70D/24F/1 high speed textured yarn in S twist or Z twist for the prevention of twisting and the maintenance of elasticity, and the said core yarn is the polyurethane series lycra soft 520 denier.

And the toe(45) and heel(46) are knitted with the core yarn single covered with polyurethane series long staple or long staple copolymer fiber as the inner threads.

One of the polyamide, polyester, or polypropylene fiber is used for the said long staple copolymer fiber.

The desirable knitting structures by parts are: 3:1 rib structure for the tightening part(41), 2:2 rib for bottom ankle(42) and first instep(43), 1; 1 rib for second instep(44) and sole (47), and solid structure for toe(45) and the heel(46).

Figure 11:
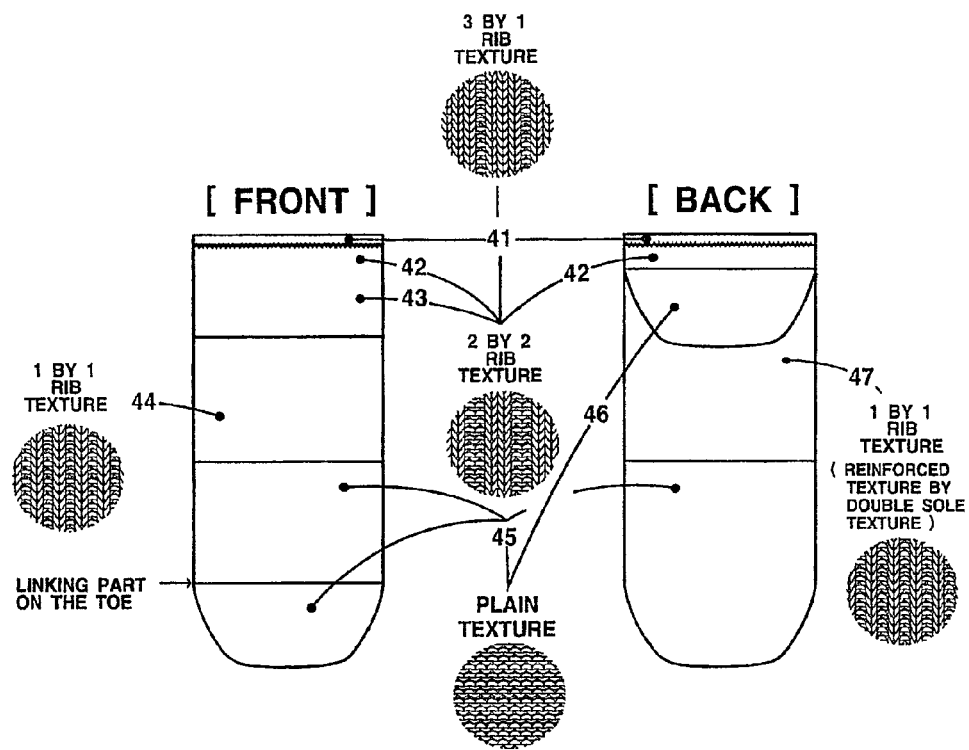
FIG. 11 illustrates a front and rear view of inside of a functional compressive nude sock produced by the art of this invention.

FIG. 11 illustrates a front and rear view of a functional compressive nude sock produced by the art of this invention.

Figure 12:
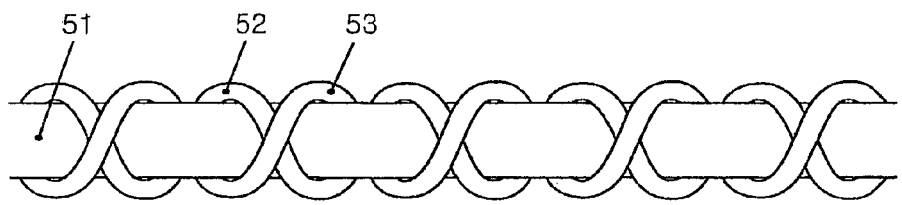
FIG. 12 illustrates a lycra soft yarn double covering processed, which is utilized in this invention.

FIG. 12 illustrates the double covered lycra soft yarn utilized in this invention, comprising the core yarn(51) and the nylon high speed textured yarn(52, 53).

As for the invention in the point of view of yarn, the core yarn(51) is a polyurethane series Lycra Soft yarn 520 denier.

Nylon high speed textured yarn(52, 53) has a good elasticity at room temperature and superior contractibility in heat process. Nylon 70D/24F/1 high speed textured yarn is used in this invention.

In order to prevent twisting and maintain elasticity after processing of the said core yarn(51), it is shown in the state of double covered with nylon 70D/24F/1 high speed textured yarn by S twist or Z twist.

As for the said double covering, first covered by S twist then by Z twist, or first covered by Z twist then covered by S twist.

Figure 13:
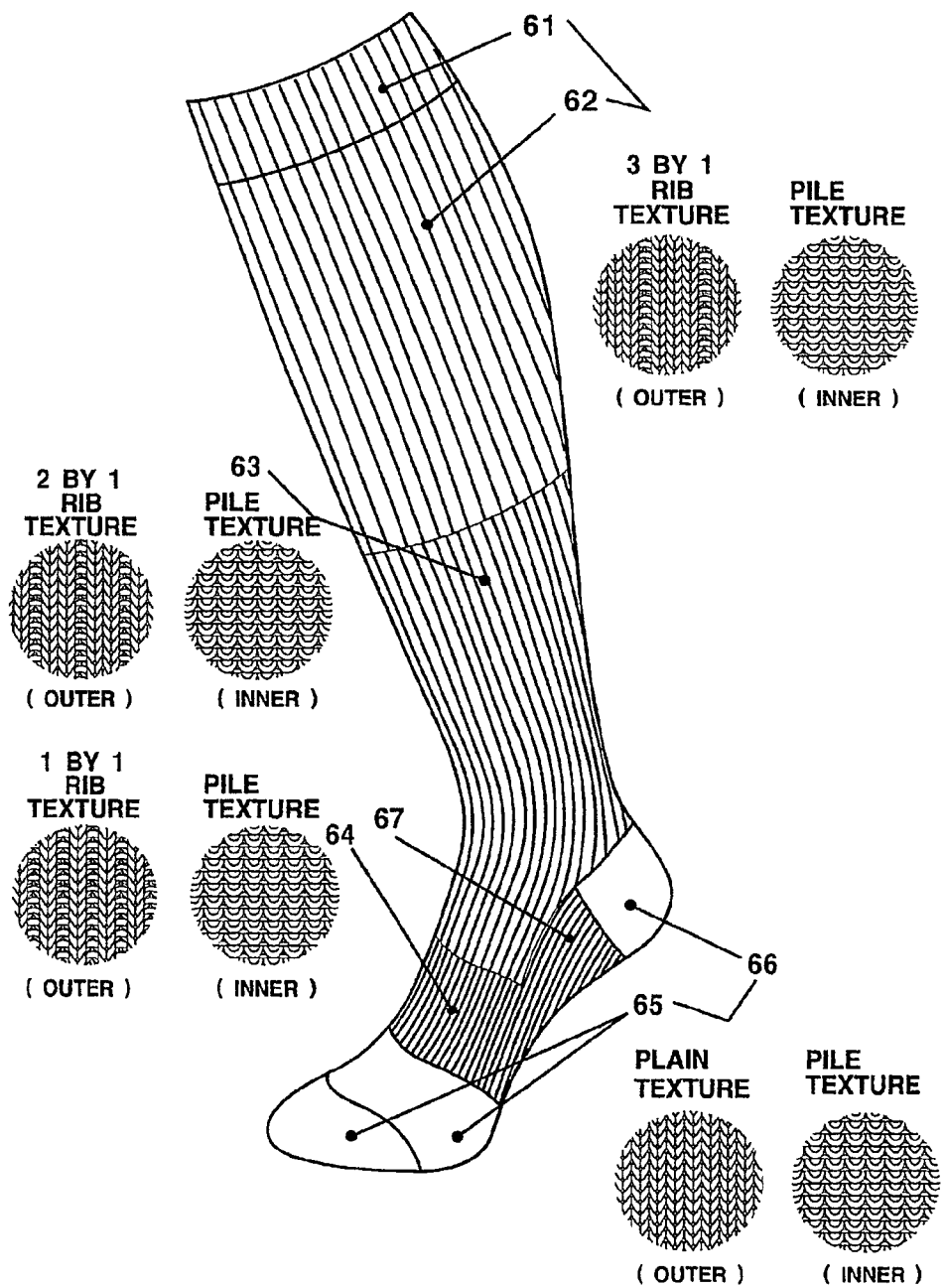
FIG. 13 illustrates an embodiment of functional compressive pile long-necked sock produced by the art of this invention.

FIG. 13 illustrates an embodiment of this invention as a functional compressive pile long-necked sock, comprising tightening part(61) at sock inlet, top shin(62), bottom shin (63), instep(64), toe(65), heel(66), and sole(67).

The tightening part(61) at the inlet, top shin(62), bottom shin(63), instep(64), and the sole(67) parts are knitted with high elastic yarn as the elastic thread and the core yarn single covered with polyurethane long staple or the long staple of copolymer fiber as the inner threads.

The said high elasticity yarn is the core yarn double covered with nylon 70D/24F/1 high speed textured yarn in S twist or Z twist for the prevention of twisting and the maintenance of elasticity, and the said core yarn is the polyurethane series lycra soft 520 denier.

And the said toe(65) and heel(66) are knitted with the core yarn single covered with polyurethane series long staple or long staple copolymer fiber as the inner threads.

One of the polyamide, polyester, or polypropylene fiber is used for the said long staple copolymer fiber.

The tightening part(61), top shin(62) are knitted in 3:1 rib structure, and inside has pile structure.

However, the inside and outside of the tightening part(61) may be knitted in 3:1 rib structure.

The bottom shin(63) is knitted in 2:1 rib structure at the outside, while knitted in pile structure inside.

The instep(64) and sole(67) are knitted in 1:1 rib structure at the outside, while knitted in pile structure inside.

The toe(65) and heel(66) are knitted in solid structure outside while knitted in pile structure inside.

Figure 14:
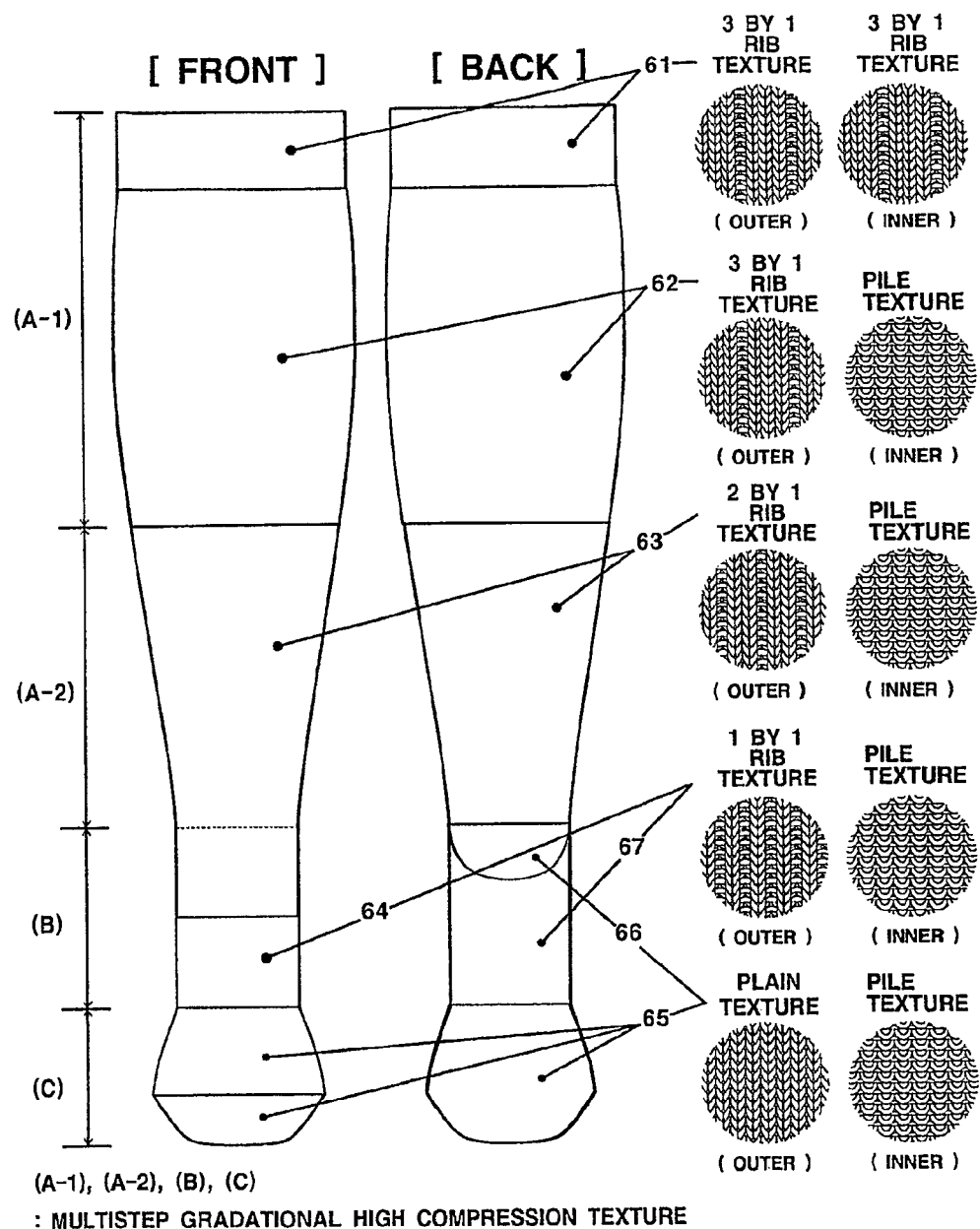
FIG. 14 illustrates a front and rear view of a functional compressive pile long-necked sock produced by the art of this invention.

FIG. 14 illustrates a front and rear view of a functional compressive pile long-necked sock produced by the art of this invention.

The reference numbers A-1, A-2, B, C represent multi stage compressive parts in accordance with the shape of leg.

Figure 15:
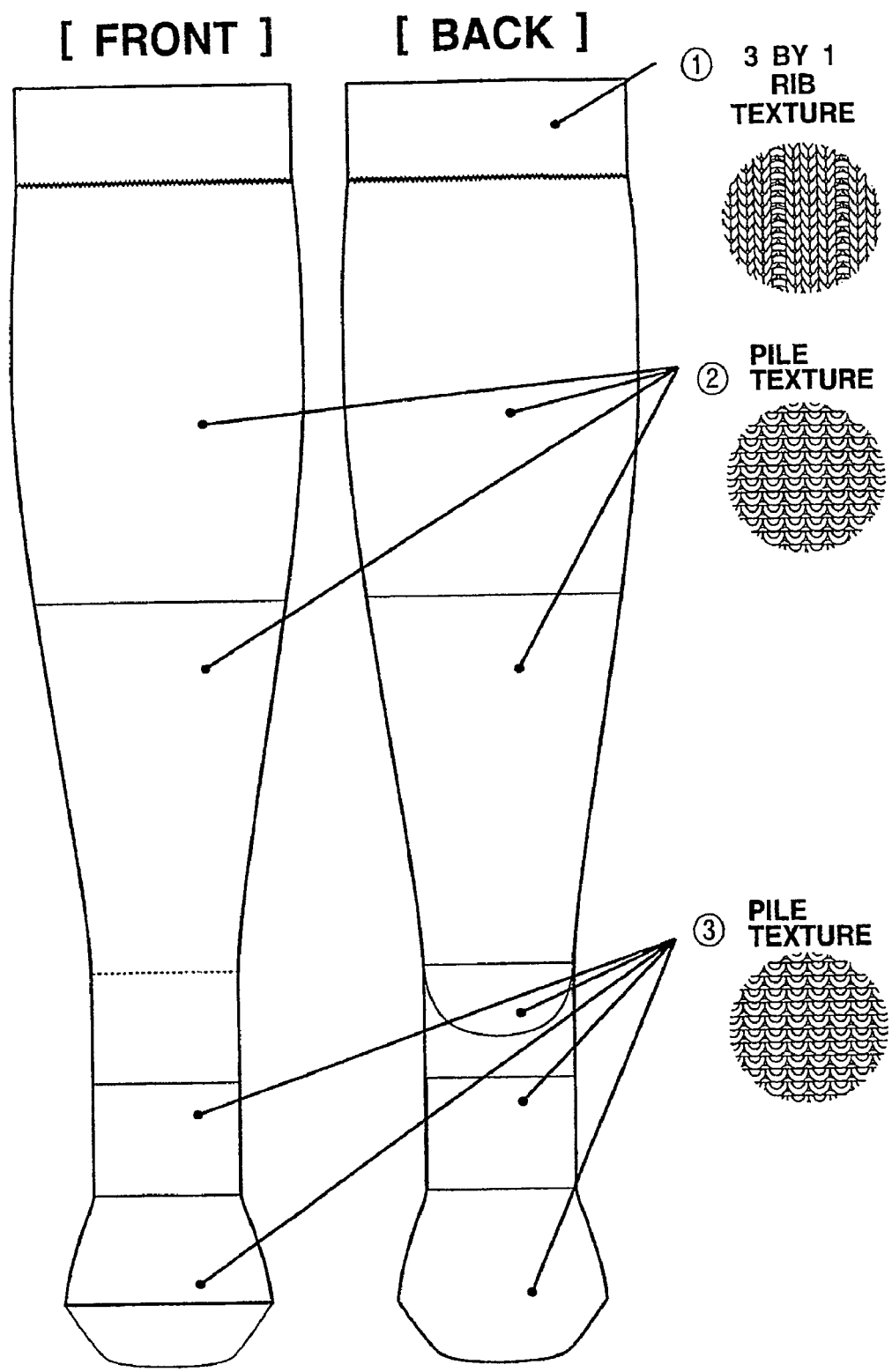
FIG. 15 illustrates a front and rear view of inside of a functional compressive pile long-necked sock produced by the art of this invention.

FIG. 15 illustrates a front and rear view of the inside of a functional compressive pile long-necked sock produced by the art of this invention.

The reference number points the tightening part which is knitted in 3:1 rib structure.

The reference numbers and points top shin, bottom shin, instep, toe, heel, and sole, which are knitted in pile structure, however, the pile structure is subject to readjustment in accordance with the use.

Figure 16:
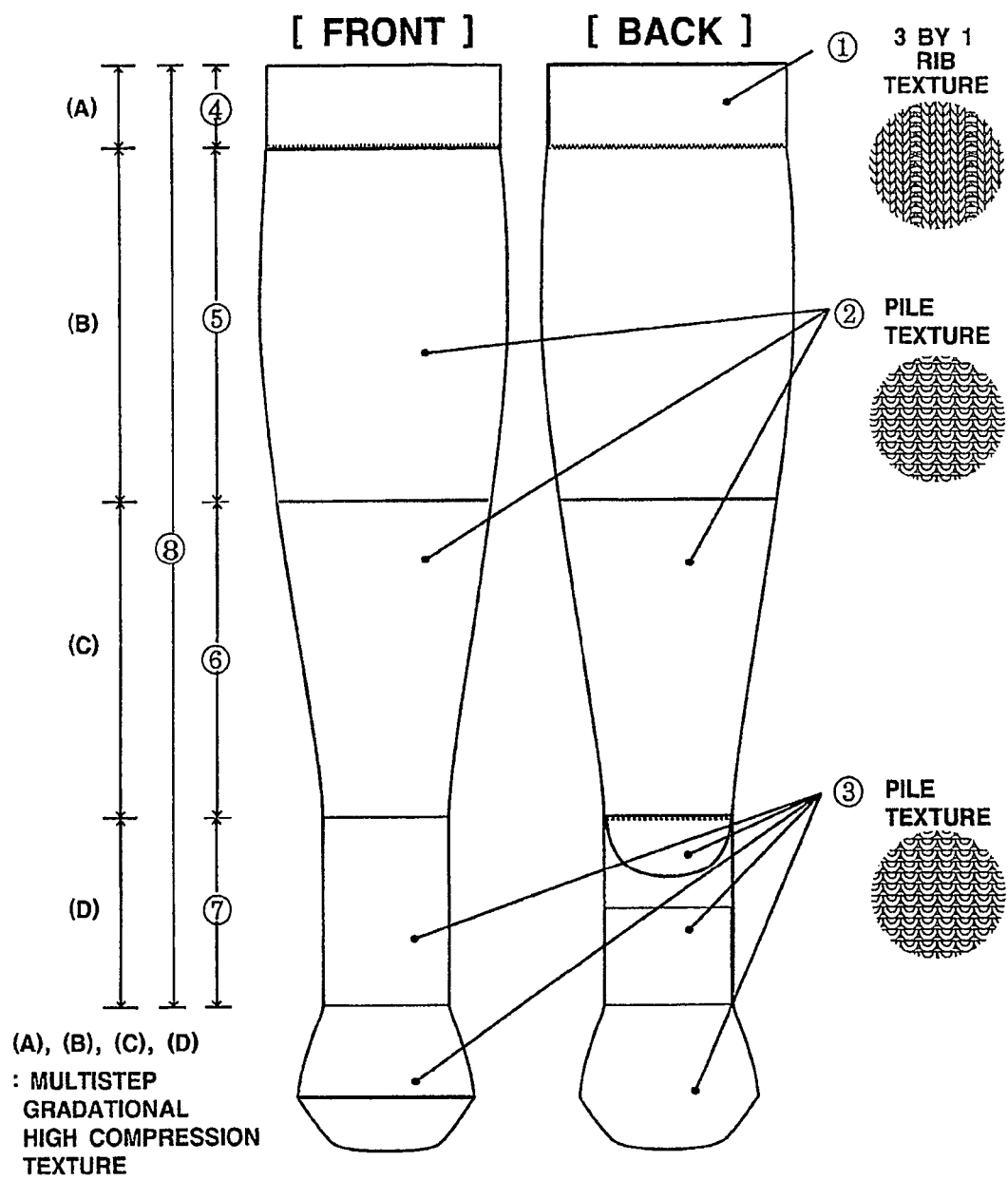
FIG. 16 illustrates a front and rear view of inside of a functional compressive pile long-necked sock produced by the art of this invention.

FIG. 16 illustrates a front and rear view of the inside of a functional compressive pile long-necked sock produced by the art of this invention.

The reference number points to the tightening part at the sock inlet, which represents the solid structure (3:1 rib), while the numbers and points the top shin, bottom shin, instep, toe, heel, and sole, representing the parts where the pile structure is. The reference numbers and symbols (A)(B)(C)(D) represent multi stage compressive parts according to the shape of leg, where the shaded parts represent parts in which high elastic yarn is used in the pile structure.

As described hereinabove, in this invention, by winding nylon 70D/24F/1 high speed textured yarn in double covering method on the lycra soft yarn at optimum conditions, which is a high elasticity core yarn, enables lycra soft, the wadding thread, maintain its characteristic elasticity, at the same time utilizes the strong restitution force which also is a characteristic of the lycra soft yarn. Consequently, the thread has two superior properties for producing socks. In addition, by applying new knitting technology and heat treatment including the piece dyeing method to enhance the elasticity of the core yarn.

And by winding nylon 70D/24F/1 high speed textured yarn on lycra soft core yarn by double covering at optimum conditions, and by being able to weave socks without using separate anti-slip yarn feeding device exclusive for polyurethane yarn, mass production at lower cost can be accomplished.

Additionally, by using said high elastic yarn, the restitution force of the lycra soft yarn can be maximized while maintaining its expansibility at an appropriate level by the application of the double covering technology in order to provide strong tightness solving the problems incurred by using latex based double covering yarns which is the most general material used for producing socks, providing a high level of physical characteristics—soft but strong restitution force.

As for the parts where the high elastic yarn is used. It is not a specific part but all over the sock that makes use of the said highly elastic yarn. The optimum tightness in accordance with the body shape is obtained by the speed control of the yarn at the sock knitting machine, implementing multi-stage compression knitting technology all over the sock except the heel and toe, propelling the blood stream in foot up to the heart. Therefore, for the knee-high socks, medical-care-type socks can be produced preventing and curing the varix and edema. This invention is characterized by utilizing the strong force of restitution and lower expansibility yarn with the implementation of multi-stage compression technology for producing socks.

As set forth hereinabove, this invention has been described referring to the embodiments illustrated in the drawings, however, such descriptions are only exemplary and explanatory, and it is obvious that anyone who has common knowledge in the field of art of this invention will be able to modify, change, or add in a wide variety not departing from the spirit and the scope of this invention as set forth in the appended claims, therefore, such modifications, changes, or additions should be considered to be covered, by and included in the claims of this invention.

INDUSTRIAL APPLICABILITY

For those who are weak at ankles, the embodiment of this invention can be quite effectively used as the ankle protective bands built in socks.

The embodiments can protect plantaris muscles, act as an artificial second skin which is highly elastic and functional that it can protect foot and skin physically.

Owing to the knitting technology enabling multi-stage elastic compression in compliance with the shape of legs, using high elasticity yarn under the control of lateral tensile force, from sole to the knees, the embodiments promote blood circulation preventing or even curing the varix and edema, and also useful for diet and body correction.

In sports activities, there will be a wide diversity of use.

As set forth hereinabove, this invention has been described referring to the embodiments illustrated in the drawings, however, such descriptions are only exemplary and explanatory, and it is obvious that anyone who has common knowledge in the field of art of this invention will be able to modify, change, or add in a wide variety not departing from the spirit and the scope of this invention as set forth in the appended claims, therefore, such modifications, changes, or additions should be considered to be covered by and included in the claims of this invention.

What is claimed is:

1. A functional compressive sock including instep, sole, heel and toe portions which are subject to mutually different and appropriate compressions, said functional compressive sock comprising:
   instep and sole portions of said functional compressive sock being knitted from a Yarn A, wherein Yarn A comprises;
      a thread of high elasticity yarn composed of a thread of 520 denier polyurethane core yarn, double-covered with nylon 70D/24F/1 high speed textured yarn; and
      an inner thread composed of at least one of,
         a thread of a polyurethane based core single covered with long staple copolymer fiber, and
         a thread of a yarn composed of long staple copolymer fiber; and
   heel and toe portions of said functional compressive sock being knitted from a Yarn B having an inner thread composed of at least one of;
      a thread of a polyurethane based core yarn single-covered with long staple copolymer fiber, and
      a thread composed of a yarn of long staple copolymer fibers.

2. The functional compressive sock according to claim 1 and further comprising shin and calf portions to form a long sock, wherein the shin, and calf portions are knitted from said Yarn A.

3. The functional compressive sock according to claim 2, wherein said long staple copolymer fiber of at least one of said Yarn A and Yarn B comprises at least one of a long staple polyamide, polyester and polypropylene yarn.

4. The functional compressive sock according to claim 2, wherein the shin and instep portions are knitted in a rib structure with a 2:2 ratio of the thread of high elasticity yarn and the inner thread in the Yarn A and the calf and sole portions are knitted in a rib structure with a 1:1 ratio of the thread of high elasticity yarn and the inner thread in the Yarn A.

5. The functional compressive sock according to claim 2, wherein the heel and toe portions are knitted as a plain knitted structure.

6. The functional compressive sock according to claim 1, wherein being a medium length sock further comprising inlet (tightening band) and ankle portions of which the inlet (tightening band), ankle, instep and sole portions are knitted from Yarn A and the toe and heel portions are knitted from Yarn B.

7. The medium length sock according to claim 6, wherein the elastic threads of high elasticity yarn of Yarn A are threads of lycra soft as a core yarn, double-covered with nylon 70D/24F/1/high speed textured yarn.

8. The medium length sock according to claim 6, wherein the long staple copolymer fibers used as the covering yarn or the base yarn of Yarn A or Yarn B is long staple polyamide, polyester or polypropylene yarn.

9. The medium length sock according to claim 6, wherein the inlet (tightening band) portion is knitted in a rib structure with a 3:1 ratio of elastic yarn and other yarn in Yarn A, the ankle portion is knitted in a rib structure with a 2:2 ratio of elastic yarn and other yarn in Yarn A, and the instep and sole portions are knitted in a rib structure with a 1:1 ration of elastic yarn and other yarn in Yarn A.

10. The medium length sock according to claim 6, wherein the heel and toe portions are knitted as a plain knitted structure.

11. The functional compressive sock according to claim 1, wherein being a short sock further comprising inlet (tightening band) and bottom ankle portions of which the inlet (tightening band), bottom ankle, instep and sole portions are knitted from Yarn A and the toe and heel portions are knitted from Yarn B.

12. The short sock according to claim 11, wherein the elastic threads of high elasticity yarn of Yarn A are threads of lycra soft as a core yarn, double-covered with nylon 70D/24F/1/high speed textured yarn.

13. The short sock according to claim 11, wherein the long staple copolymer fibres used as the covering yarn or the base yarn of Yarn A or Yarn B is Long staple polyamide, polyester or polypropylene yarn.

14. The short sock according to claim 11, wherein the inlet (tightening band) portion is knitted in a rib structure with a 3:1 ratio of elastic yarn and other yarn in Yarn A, the bottom ankle portion is knitted in a rib structure with a 2:2 ratio of elastic yarn and other yarn in Yarn A, and the instep and sole portions are knitted in a rib structure with a 1:1 ration of elastic yarn and other yarn in Yarn A.

15. The short sock according to claim 11, wherein the heel and toe portions are knitted as a plain knitted structure.

16. The functional compressive sock according to claim 1, wherein being a "nude" sock (below the ankle trainer sock) further comprising inlet (tightening band) and bottom ankle portions, wherein the instep includes first instep and second instep portions, and wherein the inlet (tightening band), bottom ankle, first and second insteps and sole portions are knitted from Yarn A and the toe and heel portions are knitted from Yarn B.

17. The "nude" sock according to claim 16, wherein the elastic threads of high elasticity yarn of Yarn A are threads of lycra soft as a core yarn, double-covered with nylon 70D/24F/1/high speed textured yarn.

18. The "nude" sock according to claim 16, wherein the long staple copolymer fibers used as the covering yarn or the base yarn of Yarn A or Yarn B is long staple polyarnide, polyester or polypropylene yarn.

19. The "nude" sock according to claim 16, wherein the inlet (tightening band) portion is knitted in a rib structure with a 3:1 ratio of elastic yarn and other yarn in Yarn A, the bottom ankle and first instep portions are knitted in a rib structure with a 2:2 ratio of elastic yarn and other yarn in Yarn A, and the second instep and sole portions are knitted in a rib structure with a 1:1 ratio of elastic yarn and other yarn in Yarn A.

20. The "nude" sock according to claim 16, wherein the heel and toe portions are knitted as a plain knitted structure.

\* \* \* \* \*